United States Patent [19]

Hotta et al.

[11] Patent Number: 4,575,251
[45] Date of Patent: Mar. 11, 1986

[54] MEASUREMENT DEVICE OF PHOTOGRAPHIC DENSITY OF FILM

[75] Inventors: Tomiji Hotta, Kyoto; Mitsuo Inoue, Ōtsu, both of Japan

[73] Assignee: Dainippon Screen Mfg. Co., Ltd., Kyoto, Japan

[21] Appl. No.: 552,450

[22] Filed: Nov. 16, 1983

[30] Foreign Application Priority Data

Dec. 11, 1982 [JP] Japan .................. 57-218169

[51] Int. Cl.⁴ ............................................ G01N 21/59
[52] U.S. Cl. ...................................... 356/443; 250/559; 250/571; 356/429
[58] Field of Search ................ 356/443, 444, 432, 435, 356/404, 243, 433–434, 429–431; 354/298; 355/68; 250/559, 571

[56] References Cited

U.S. PATENT DOCUMENTS

| | | | |
|---|---|---|---|
| 3,709,613 | 1/1973 | Zahn et al. | 356/443 |
| 3,787,689 | 1/1974 | Fidelman | 354/298 |
| 3,995,959 | 12/1976 | Shaber | 250/559 X |
| 4,061,428 | 12/1977 | Amano et al. | 356/435 X |
| 4,345,831 | 8/1982 | Kachelries | 356/444 X |
| 4,370,558 | 1/1983 | Kinoshita et al. | 356/443 X |

FOREIGN PATENT DOCUMENTS

| | | |
|---|---|---|
| 50-27544 | 3/1975 | Japan . |
| WO82/01940 | 6/1982 | PCT Int'l Appl. . |
| 1078182 | 1/1965 | United Kingdom . |

Primary Examiner—Vincent P. McGraw
Assistant Examiner—Robert D. V. Thompson, III
Attorney, Agent, or Firm—Brumbaugh, Graves, Donohue & Raymond

[57] ABSTRACT

In a measurement device of photographic density of a film wherein a light source is provided on one side over a film carrier route and a plurality of light receiving elements for converting transmitted light of a film emitted from the said light source to an electrical signal are provided on the counter side of the light source forming a line, a device for measuring photographic density of the film comprising a means for obtaining a rate of change in the form of a ratio between a reference signal decided beforehand for each of the light receiving elements and an output signal of the light receiving elements when the film is carried, and a means for obtaining photographic density of the film in accordance with the obtained ratio.

2 Claims, 2 Drawing Figures

MEASUREMENT DEVICE OF PHOTOGRAPHIC DENSITY OF FILM

BACKGROUND AND SUMMARY OF THE INVENTION

The present invention relates to apparatus by which the photographic density of a developed film is photoelectrically measured.

Generally in a photographic film processor, in order to recover the activity of a developer or developing solution once declined after the process of development, a new developer or replenisher is to be replenished. Particularly in the film processor for lithographic film or the like which requires high accuracy, since the result of the development is considerably influenced by the under or over replenishment of the developer, the replenishment is controlled in accordance with the measured value obtained through measuring the photographic density of the developed film.

Concerning the measuring method of photographic density of a film, as exemplified in Japan Patent Application laid open under No. 56-154650, a method is known wherein a linear light source is arranged on one side across a carrier route of the film and a linear light receiver is oppositely arranged on the counter side respectively, thereby measuring a quantitative difference between an incident light to the light receiver when there is no film between the light source and the light receiver and the incident light when the film is carried through between the light source and the light receiver. In this method, however, measurement error is serious since only the average photographic density in rather wide area can be measured.

On the other hand, as exemplified in Japan Patent Application laid open under No. 50-27544, another attempt is proposed wherein a plurality of light receiving elements are arranged at equal spacing therebetween in place of the linear light receiver so as to scan the film carried and to make integral addition of the output signals from each of the light receiving elements altogether, thereby measuring photographic density. In this method, it is necessary to straighten the light receiving characters of the plurality of the light receiving elements arranged across the carrier route, and accordingly it is also necessary to adjust the sensitivity of the plurality of light receiving elements one by one when assembling thereof. However, it is quite difficult to get a linear light source emitting an uniform quantity of light over the full length thereof, and besides it takes long for the adjustment. Consequently, it may be said that the wider the measuring width of the film or the more the number of light receiving element, the more difficult the said adjustment.

Further, in the conventional measurement device of photographic density of a film, it is generally adjusted not to replenish the developer when the photographic density is under 5% approx. This is because, even in case of a transparent film, the transmission of light is usually impeded by 5% or so, and because, without such adjustment, the replenishment will be unnecessarily effected even to the transparent film not bearing the photographic density at all yet. In the said conventional measurement device with adjustment as above-described, however, when a film having a narrower width than the effective measuring width and having rather smaller photographic density area is applied to the measurement device, or as an extreme case when a film having its width less than 5% of the effective measuring width and already bearing a full photographic density is applied thereto, so far as the measured value is under 5%, the replenishment is not carried out in spite of already bearing the photographic density, resulting in the aggravation of the development process thereafter.

It is, therefore, an object of the present invention to provide a measurement device for exactly measuring photographic density of a film without foregoing adjustment as well as irrespective of the width of the applied film by obtaining a rate of change in the form of a ratio between the reference signal decided immediately before carrying the film and the actual output signal of the light receiving element when the film is carried.

Thus, in accordance with the present invention, there is provided, in a measurement device of photographic density of a film wherein a light source is provided on one side over a film carrier route and a plurality of light receiving elements for converting the transmitted light of a film emitted from the said light source to an electrical signal are provided on the counter side of the said light source forming a line, a device for measuring photographic density of the film comprising a means for obtaining a rate of change in the form of a ratio between a reference signal decided beforehand for each of the light receiving elements and an output signal of the light receiving elements when the film is carried, and a means for obtaining photographic density of the film in accordance with the said ratio.

More particularly, by the foregoing formation, the present invention contemplates a measurement device of photographic density of a film having its advantages and features as follows:

(i) By adding the rate of change between the reference signal and the output signal of the light receiving elements after being obtained the said rate in the form of a ratio, it is neither necessary to straighten the light receiving characters of each of the light receiving elements being different from the conventional method, nor necessary to have a light source whose quantity of light must be uniform over the full length.

(ii) Even in case of the photographic density in the width under 5% of the effective measuring width of an automatic developing machine, the replenishment is exactly carried out through measuring each of the light receiving elements.

(iii) When the reference signal is obtained, by taking an arithmetic mean of several output signals, the change in the quantity of light can be appropriately adjusted, and further by making compensation at the interval of every 5 seconds, for example, the said change can be more effectively controlled.

(iv) As the output signal is monitored for each of the light receiving elements, even in case of a failure in some of the light receiving elements, the control can be made without difficulty.

Other objects, features and advantages of the present invention will become apparent in the cource of the following description with the accompanying drawings.

BRIEF DESCRIPTION OF THE DRAWINGS

In the accompanying drawings, forming a part of the present invention, and in which like parts are designated reference numerals or characters throughout the same.

DESCRIPTION OF THE PREFERRED EMBODIMENTS

Figure 1:
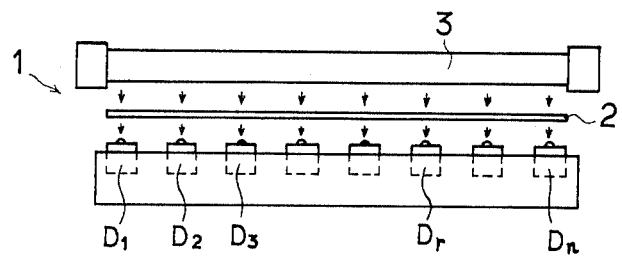
FIG. 1 is a front view showing a detection part of a measurement device of photographic density of a film embodied in accordance with the present invention.

Referring now to FIG. 1 showing a detection part 1 of a measurement device of photographic density of a film in accordance with the present invention, a film 2 which has already completed the development process is carried to the next process in the direction of a right angle to the paper surface, and at some discretional positions of the carrier route of the film 2, there is provided a light source 3 on one side over the carrier route and are also provided a plurality of light receiving elements D1 thru Dn oppositely on the counter side of the light source 3 forming a line. The said light source has its length over the full width of the film 2, and in this formation it is not always necessary to be formed as a single source it being permitted to provide a plurality of light emitting diodes or the like forming a line. The light receiving elements D1 thru Dn are used for photoelectrically detecting the photographic density of the film 2, and comprise photodiodes or phototransistors, said plurality of elements are provided in parallel to the light source 3 at the positions of the counter side thereof with the predetermined spacing and forming a line over the full width of the film 2.

Figure 2:
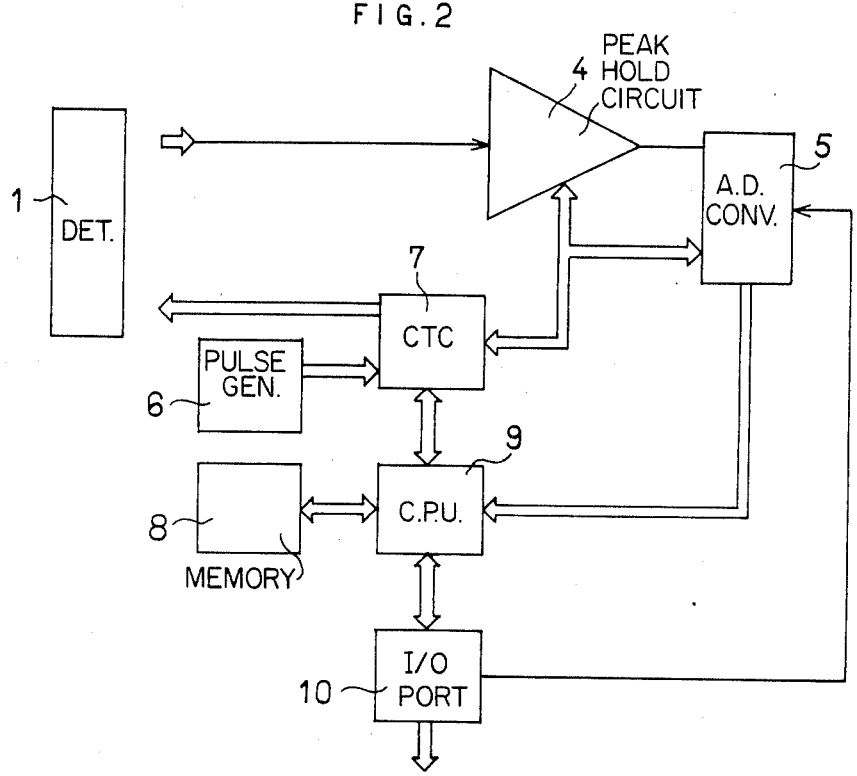
FIG. 2 is a block diagram of an electrical wiring of the said device.

Referring to FIG. 2 showing a block diagram of the electrical wiring of the measurement device of photographic density of a film, when the film 2 has not yet entered in the detection part 1, signals from each of the light receiving elements D1 thru Dn generated before the entrance of the film, are input to a peak hold circuit 4 synchronizing with pulse signals generated from a counter timer controller 7 (hereinafter called as "CTC").

The peak hold circuit 4 is used for simple A/D conversion, and the signals run from the peak hold circuit 4 through an A/D converter 5 to be input to a central process unit 9 (hereinafter called as "CPU") as 8 bits units, for example. Then, with respect to the signals input to the CPU 9, an arithmetical mean is taken for each of the light receiving elements D1 thru Dn together with the signals previously input thereto in the same manner (if there exists no such signal, it is reinput), and the result of the said arithmetical mean is memorized to a memory 8 as a reference signal A. The sensitivity of each of the light receiving elements D1 thru Dn of the detection part 1 is subject to changes caused by the temperature changes, dust, etc., however, in order to meet such a change, the foregoing action or operation is repeated every 5 seconds, for example, and up to the moment when the CPU 9 perceives or judges the entrance of the film 2 in the detection part 1, the reference signal A is continuously compensated all the time.

When the film 2 enters in the detection part 1 and any of the light receiving elements D1 thru Dn detects a value of photographic density exceeding 5% which is equivalent to the damping factor of the light of a transparent film, the CPU 9 judges that the film 2 has entered in the detection part 1. However, if only one light receiving element Dr detects a photographic density exceeding 5% continuously for a while, when the remaining light receiving elements other than the light receiving element Dr do not detect any photographic density at all, it is assumed that the entrance of the film has not yet accured, and instead that the element Dr is out of order.

Meanwhile, pulses generated from a pulse generator 6 provided on a driving part of the film carrier are continuously transmitted to the CTC 7 corresponding to the rotation speed of the driving motor (not illustrated), and when the film 2 has entered in the detection part 1, the said pulses are transmitted to the detection part 1 through the CTU 7 by the control of the CPU 9. And in the detection part 1, the film 2 is scanned for each of the said pulses, and an output signal B for each of the light receiving elements D1 thru Dn is input to the CPU 9 through the peak hold circuit 4 and the A/D converter 5. The CPU calculates or obtains a rate of change for each of the light receiving elements in the form of a ratio $(A-B)/A$ between the light receiving elements corresponding to the photographic density exceeding 5% of the said output signal B and the reference signal A of the corresponding light receiving elements previously memorized, and adding every ratio altogether, the result is memorized to the memory 8 as a data of the photographic density.

In this connection, as the damping factor of the light of the film not bearing photographic density is 5% approx., regarding the light receiving elements on which the damping factor less than 5% is detected, the addition is not effected defining that there exists no photographic density. In other ward, when $0.95A-B$ is negative, no such adding calculation is operated. Further, in order to make the said ratio $(A-B)/A$ more accurate, putting the damping factor of the light of the film not bearing photographic density as a%, the following equation can be applied:

$$\frac{\frac{100-a}{100}A - B}{\frac{100-a}{100}A},$$

namely, to this effect, the reference signal A can be replaced with $$\frac{100-a}{100}A.$$

Then with the advance of the film 2 the above-described action or operation is repeated and when the memorized data of photographic density mounts to a certain value, a replenishment signal is output from the CPU 9 through an input/output port 10, thus resulting in the replenishment in accordance with the memorized data.

In the foregoing description, although the damping factor of a transparent film not bearing photographic density is illustratively fixed or supposed to be 5%, this value can be changed depending upon the proper damping factor of a film as a matter of course.

Further, in the foregoing description, although the photographic density is described from the view point of the volume thereof, in case of the application to the lithographic film or the like, as the result of development becomes either deep black or not alternatively, the photograpgic density can be replaced with the area thereof in place of the volume also as a matter of course.

While the above-described embodiment represents the preferred form of the present invention, it is to be understood that modifications will occur to those skilled in the art without departing from the spirit of the present invention. the scope of the present invention is, therefore, to be determined solely by the appended claims.

What is claimed is:

1. Apparatus for measuring the photographic density of a film wherein the film is passed between a light source and a plurality of light sensitive elements for converting the received light into electrical signals comprising;
    means supplied with the electrical signals in the absence of film for deriving an arithmetic average value A of said electrical signals,
    means supplied with the electrical signals in the presence of film for deriving a value B and in turn the value $(A - B_n)$ for each element,
    and means for summing the $(A - B_n)/A$ values for all the elements for deriving the desired measure for utilization.

2. Apparatus in accordance with claim 1 in which there is substituted for the value A the value $$\frac{100 - a}{100} A$$

where a is the damping factor of film not having photographic density, and there is derived the value $$\frac{\frac{100 - a}{100} A - B_n}{\frac{100 - a}{100} A}$$

for each element, and these values are summed for all elements for deriving the desired measure for utilization.

* * * * *